(12) United States Patent
Shoham (10) Patent No.: US 9,655,649 B2
(45) Date of Patent: May 23, 2017

(54) SPINAL FUSION USING RODS OF SHAPE MEMORY MATERIAL

(75) Inventor: Moshe Shoham, M.p Hamovil (IL)

(73) Assignee: MAZOR ROBOTICS LTD., Caesarea (IL)

( * ) Notice: Subject to any disclaimer, the term of this patent is extended or adjusted under 35 U.S.C. 154(b) by 1801 days.

(21) Appl. No.: 11/703,923

(22) Filed: Feb. 7, 2007

(65) Prior Publication Data
US 2007/0162007 A1 Jul. 12, 2007

Related U.S. Application Data

(63) Continuation-in-part of application No. PCT/IL2005/000875, filed on Aug. 12, 2005.

(60) Provisional application No. 60/601,110, filed on Aug. 13, 2004.

(51) Int. Cl.
| | |
|---|---|
| *A61B 17/56* | (2006.01) |
| *A61B 17/70* | (2006.01) |
| *A61B 17/00* | (2006.01) |

(52) U.S. Cl.
CPC ...... *A61B 17/7002* (2013.01); *A61B 17/7083* (2013.01); *A61B 17/7089* (2013.01); *A61B 2017/00867* (2013.01)

(58) Field of Classification Search
CPC ............... A61B 17/7089; A61B 18/02; A61B 2018/00005; A61B 2017/00867; A61F 2002/4653; A61F 2002/4654; A61F 2002/4655
USPC ................... 606/250–263, 299, 911
See application file for complete search history.

(56) References Cited

U.S. PATENT DOCUMENTS

| | | | |
|---|---|---|---|
| 4,697,582 A | | 10/1987 | William et al. |
| 5,037,427 A | * | 8/1991 | Harada et al. ................ 606/108 |
| 5,290,289 A | * | 3/1994 | Sanders et al. ............... 606/279 |
| 5,540,689 A | * | 7/1996 | Sanders et al. ............... 606/276 |
| 5,551,871 A | * | 9/1996 | Besselink et al. ................ 433/5 |
| 5,586,983 A | * | 12/1996 | Sanders et al. ............... 606/277 |

(Continued)

FOREIGN PATENT DOCUMENTS

| | | | | |
|---|---|---|---|---|
| EP | 0470660 A1 | * | 12/1992 | .................. 606/86 A |
| WO | 2006016371 | | 2/2006 | |

OTHER PUBLICATIONS

Publication entitled "Medtronic CD Horizon Sextant fact sheet" printed from www.medtronicsofamordanek.com on Oct. 5, 2016.

(Continued)

*Primary Examiner* — Ellen C Hammond
(74) *Attorney, Agent, or Firm* — Fish & Richardson P.C.

(57) ABSTRACT

A system and method for performing spinal fusion using vertebral connecting rods constructed of a shape memory material, such as shape memory alloy. The connecting rod is cooled below its phase transition temperature, which is chosen to be just below body temperature, and is inserted through a curved guide tube previously inserted into the back of the patient. The guide tube is located so as to deliver the connecting rod at its desired location between the preinserted pedicle screw heads. The rod, being in its flexible state below the transition temperature, negotiates the curve and exits the guide tube in a straight form and parallel to the patient's spine. As it heats up to body temperature, it regains its original straight shape and its original rigidity, and is ready for connecting its associated vertebrae to each other.

15 Claims, 4 Drawing Sheets

(56) References Cited

U.S. PATENT DOCUMENTS

| | | | |
|---|---|---|---|
| 5,658,286 A | 8/1997 | Sava | |
| 5,728,098 A * | 3/1998 | Sherman et al. | 606/269 |
| 5,766,004 A * | 6/1998 | Besselink et al. | 433/5 |
| 5,772,627 A * | 6/1998 | Acosta et al. | 604/22 |
| 5,779,707 A * | 7/1998 | Bertholet et al. | 606/75 |
| 5,989,208 A * | 11/1999 | Nita | 604/22 |
| 5,989,280 A * | 11/1999 | Euteneuer et al. | 623/1.1 |
| 6,210,413 B1 * | 4/2001 | Justis et al. | 606/254 |
| 6,235,028 B1 * | 5/2001 | Brumfield et al. | 606/53 |
| 6,273,888 B1 * | 8/2001 | Justis | 606/272 |
| 6,296,644 B1 * | 10/2001 | Saurat et al. | 606/256 |
| 6,387,130 B1 * | 5/2002 | Stone et al. | 623/17.16 |
| 6,488,683 B2 * | 12/2002 | Lieberman | 606/263 |
| 6,558,386 B1 | 5/2003 | Cragg | 606/279 |
| 7,267,687 B2 * | 9/2007 | McGuckin, Jr. | 623/17.11 |
| 7,320,686 B2 * | 1/2008 | Serhan et al. | 606/90 |
| 7,976,568 B2 * | 7/2011 | Cheung et al. | 606/279 |
| 2002/0029039 A1 * | 3/2002 | Zucherman et al. | 606/61 |
| 2002/0198526 A1 * | 12/2002 | Shaolian et al. | 606/61 |
| 2003/0191470 A1 * | 10/2003 | Ritland | 606/61 |
| 2003/0216739 A1 * | 11/2003 | Ip et al. | 606/72 |
| 2004/0034351 A1 * | 2/2004 | Sherman et al. | 606/61 |
| 2004/0215191 A1 * | 10/2004 | Kitchen | 606/61 |
| 2004/0215192 A1 * | 10/2004 | Justis et al. | 606/61 |
| 2004/0260305 A1 * | 12/2004 | Gorensek et al. | 606/99 |
| 2005/0033295 A1 * | 2/2005 | Wisnewski | 606/61 |
| 2005/0065516 A1 * | 3/2005 | Jahng | 606/61 |
| 2005/0090899 A1 * | 4/2005 | DiPoto | 623/17.11 |
| 2005/0124991 A1 * | 6/2005 | Jahng | 606/61 |
| 2005/0131405 A1 * | 6/2005 | Molz et al. | 606/61 |
| 2005/0154390 A1 * | 7/2005 | Biedermann et al. | 606/61 |
| 2005/0277934 A1 * | 12/2005 | Vardiman | 606/61 |
| 2006/0149238 A1 * | 7/2006 | Sherman et al. | 606/61 |
| 2007/0162007 A1 * | 7/2007 | Shoham | 606/61 |
| 2007/0173828 A1 * | 7/2007 | Firkins et al. | 606/61 |
| 2007/0250038 A1 * | 10/2007 | Boulais | 604/523 |
| 2008/0004528 A1 * | 1/2008 | Fitzsimons et al. | 600/439 |
| 2008/0234738 A1 * | 9/2008 | Zylber et al. | 606/254 |
| 2009/0048632 A1 * | 2/2009 | Firkins et al. | 606/246 |
| 2009/0088803 A1 * | 4/2009 | Justis et al. | 606/254 |
| 2009/0222042 A1 * | 9/2009 | Firkins et al. | 606/246 |
| 2009/0287060 A1 * | 11/2009 | Pell et al. | 600/201 |
| 2010/0063548 A1 * | 3/2010 | Wang | 606/279 |
| 2010/0241120 A1 * | 9/2010 | Bledsoe et al. | 606/62 |
| 2011/0077687 A1 * | 3/2011 | Thompson et al. | 606/254 |
| 2012/0078315 A1 * | 3/2012 | Sweeney | 606/86 A |
| 2013/0317303 A1 * | 11/2013 | Deshmukh et al. | 600/202 |
| 2014/0276758 A1 * | 9/2014 | Lawrence et al. | 606/33 |

OTHER PUBLICATIONS

Ahmet Levent Aydin, et al., Percutaneous Transpedicular Screw Insertion Technique (Sextant), Minimally Invasive Procedures in Spine Surgery, Jan. 2005, p. 141-147.

Kevin Foley, et al., CD Horizon Sextant II, Rod Insertion System manual published by Medtronic Sofamor Danek USA, Inc., 2005, p. 1-46.

Keven Foley, Rod Insertion System Surgical Techniques, Sales manual issued in Jun. 2003 by Medtronic for the CD Horizon Sextant.

M.M.M. Eldin, et al., Percutaneous Transpedicular Fixation: Technical Tips and Pitfalls of Sextant and Pathfinder Systems, published in Jan. 2016 in Asian Spine Journal, vol. 10(1), p. 111-122.

* cited by examiner

SPINAL FUSION USING RODS OF SHAPE MEMORY MATERIAL

CROSS-REFERENCES TO RELATED APPLICATIONS

This application is a continuation-in-part of PCT Application no. PCT/IL2005/000875, filed Aug. 12, 2005, which claims the benefit of U.S. Provisional Patent Application 60/601,110 filed Aug. 13, 2004 the disclosure of both are incorporated herein by reference in their entirety.

FIELD OF THE INVENTION

The present invention relates to the field of spinal fusion using connecting rods, and especially to connecting rods that can be inserted by minimally invasive procedures.

BACKGROUND OF THE INVENTION

Vertebral fusion is a common spinal surgical procedure, performed in order to overcome problems related to impaired mutual interaction between neighboring vertebrae. The technique involves the disablement of the relative mechanical motion between adjacent vertebrae, the stimulating of growth of inter-vertebra hard tissue, causing the two vertebrae to fuse and thus preventing compression during body movements and stabilizing the spinal column. Spinal fusion is a very common procedure, with an estimated over 400,000 procedures performed annually in the USA alone.

Figure 1:
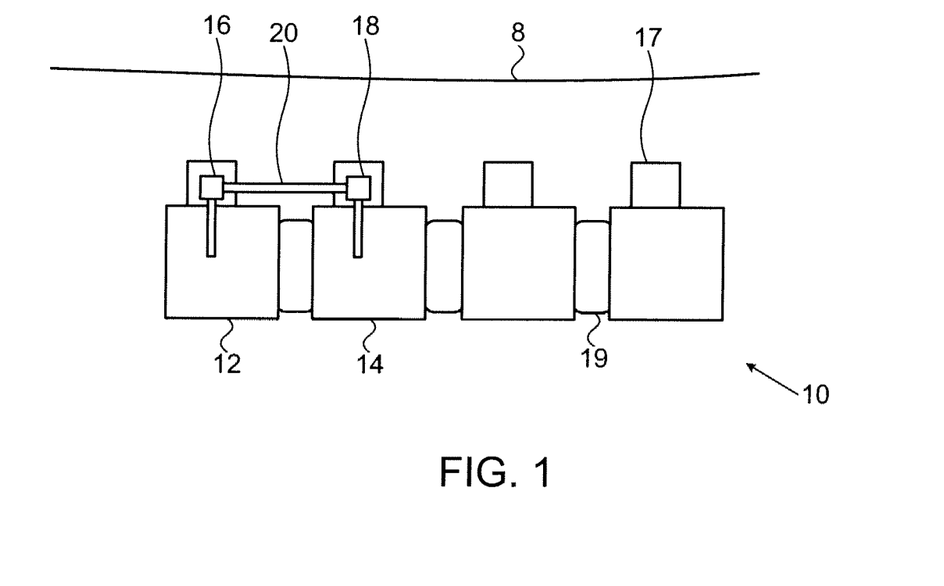
FIG. 1 is a schematic illustration of a side view of a spine with an adjacent pair of vertebrae fused using two pedicle screws and a connecting rod.

A common method for fusing two vertebrae is by means of connecting rods, one on either side of the spine, each rod connecting two pedicle screws inserted into the pedicles of the two adjacent vertebrae. The rods are generally inserted into slots in the heads of the pre-inserted pedicle screws. Thus, in order to fuse one level, by which is meant two adjacent vertebrae, two rods, one on either side of the spine, are generally affixed to the vertebrae by means of screws inserted into the four pedicles involved, and thus connect the vertebrae rigidly, as shown in FIG. 1. There also exists a technique, known as the Dynesys® Dynamic Stabilization System, supplied by Zimmer Inc., of Warsaw, Ind., by which slight relative motion between neighboring vertebrae is maintained by the use of slightly flexible polymer connecting tubes attached to pedicle screws by means of a polyethylene cord.

The connecting rods are aligned along the spine axis, so that in a conventional open surgical procedure, an incision of about the same length of the rods has to be made in order to insert the rods and to connect them between the two vertebrae. In an adult, this generally involves an incision of at least 50 mm, generally made at the middle line, and lateral access to insert the rods is obtained by stretching of the soft tissue.

Recently, minimally invasive procedures have been developed in order to minimize the extent of the cut and still to enable insertion of the rods. For example, the CD HORIZON© SEXTANT™ Percutaneous Rod Insertion Set, supplied by Medtronic Inc., of Minneapolis, Minn., enables the insertion of a curved rod along an arc that becomes tangential to the direction of the spine in the region of the pedicle screws. The advantage is that only three small incisions on each side of the spine are required in the skin itself, two for the two legs of the SEXTANT™ and one for the entry point of the rod of the SEXTANT™ itself, but a long cut is still necessary under the skin in order to insert the rod. The length of this subcutaneous cut is necessary because of the limitation that the rod has to have a shallow arc between the pedicles, and such a large diameter arc requires a comparatively long curved pathway within the tissues of the back for its insertion.

Another procedure is that provided by Spinal Concepts Inc. of Austin, Tex., called PathFinder™ Minimally Invasive Surgery Pedicle Screws, in which an incision in the skin is made, into which a slotted guide is fitted. The rigid connecting rod is inserted down this guide and tilting during insertion to be parallel to the spine. The lower end is worked towards the further pedicle screw, spreading the soft tissue in front of its path. Spreading of tissue is assumed to be less invasive than cutting to the same extent.

However, although these prior art systems are less invasive than the classical open incision methods traditionally used, they still involve tissue and muscle trauma beyond that of simple incisions of limited size. There therefore exists a need for an even less invasive method for performing spinal fusion procedures than those currently available.

The disclosures of each of the publications mentioned in this section and in other sections of the specification, are hereby incorporated by reference, each in its entirety.

SUMMARY OF THE INVENTION

The present invention seeks to provide a new method and apparatus by which spinal fusion can be performed in a manner less invasive than possible using the above-described prior art methods. According to the present invention, use is made of vertebral connecting rods made of a material which changes its rigidity as a function of temperature, with the change taking place in a temperature region just below that of body temperature. One such group of materials is known as Shape Memory Alloys (hereinafter abbreviated to SMA), whose crystalline structure undergoes a phase change from austenitic to martensitic when cooled through the range of temperatures over which the phase transformation occurs, and vice versa as the material is heated up over the transition temperature range. In the austenitic phase, SMA's have rigid properties, with good material strength. In the martensitic phase, SMA's are readily deformable, the level of flexibility depending on the particular SMA used. While in the martensitic phase, such SMA materials can be readily bent into shapes very different from their original shape. In addition, such materials show shape memory, in that, regardless of the shape into which the material is bent below its transition point, it will return not only to its original rigidity when its temperature rises above the transition temperature, but also to the original shape into which it was annealed before being cooled. The phase change from martensitic to austenitic phase (and vice versa) can be selected to be somewhat below body temperature, or even below room temperature, depending on the particular SMA composition chosen.

In order to use the vertebral fusion system of the present invention, pedicle screws are first inserted into the relevant vertebrae, in a minimally invasive manner. Then, in accordance with a preferred embodiment of the present invention, a curved tube is inserted into an incision in the patient's back, until its inserted end is located close to one of the pedicle screw heads to which the connecting rod is to be attached. The tube can be inserted through an opening no larger than the diameter of the tube, such that the incision can be small. A connecting rod made of an SMA material, and cooled to below its transition point, is inserted down the tube, and, because of its flexibility below its transition point, readily negotiates the curved end of the tube, to exit the tube in a direction essentially parallel to the spine. Once it has exited the delivery tube, the SMA rod heats up by contact with the body tissue around it, switches phase to its rigid state, and at the same time, regains its original straight form as a result of the shape memory effect. Once in this state, it can be pushed through the tissue and muscle between the vertebrae after exiting the end of the tube, until it reaches its final intended position between the pedicle screw heads. It is then attached to the pedicle screw heads preferably in the conventional manner using set screws, and the insertion tube is then withdrawn. The delivery tube is preferably left in position until after the connecting rod has been firmly attached to the pedicle screws, in order to provide additional support to the rod during the tightening procedure.

There exist prior art uses of shape memory materials in the medical field, such as in stents, cage hooks, bone support structures, compression clamping devices, and the like. However, these prior art applications generally involve a device having one defined shape outside the body when cooled, and when heated by the body after insertion, they regain their original pre-cooling shape, which is different from the cooled shape before insertion. Usually, such prior art devices are formed into a collapsed or compressed shape when cooled, in order to enable their insertion into the body through a small opening in this collapsed or compressed state. On warming up after insertion, they regain their larger memory shape. In contrast to such prior art applications, the connecting rods of the present invention must change their shape during the process of passing into the body during the insertion phase, since it is just this change of shape which enables their insertion in such a non-invasive manner. This change of shape during insertion is enabled by the change in flexibility of the shape memory material. The final warm shape, which is the memory shape, must be of the shape and stiffness required, but the initial cooled shape and the final warm shape can be identical. In this respect, the connecting rods of the present invention undergo a dynamic process during insertion, unlike the switch between two static states used in prior art devices. This feature of the rods of the present invention, namely that the final shape of the insert after insertion need be no different from its shape before insertion, and that the special properties of the shape memory material are used to facilitate the insertion of the insert, can be utilized, according to further preferred embodiments of the present invention, for providing such inserts for use in other medical applications.

In using the vertebral fusion system of the present invention, only small incisions are required either side of each vertebra for inserting the pedicle screws. According to one preferred embodiment, the curved delivery tube can be inserted through this same incision, and maneuvered into its correct position by stretching the tissue around the incision hole to get to the correct position for delivery of the connecting rod. According to another preferred embodiment, an additional small incision is made near each pedicle screw insertion incision, and the delivery tube inserted through this additional hole. Thus, according to either of these embodiments, the invasiveness of the procedure is substantially reduced, even compared to the above-mentioned minimally invasive methods.

In addition to SMA's, which are metallic materials, shape memory polymers (SMP's) have also recently been developed, though their range and properties are less extensive than those of SMA's. Such shape memory polymers have somewhat different characteristics to those of SMA's, but a transition temperature, known as the glass transition temperature, tailored to be around body temperature, and below which SMP's have highly elastic properties, may make them suitable candidates for use as spinal fusion connecting rods inserted using the methods and system of the present invention. Since SMP's, being plastic materials, are generally more flexible in their rigid state than the metallic SMA's, such SMP's could provide a slight level of relative motion between vertebrae, as is supplied by the Dynesys® system mentioned above.

According to another preferred embodiment of the present invention, use is made of another property of SMA's, known as pseudo-elasticity, or super-elasticity. This is a property of the austenitic phase of SMA's, whereby the application of stress, without any temperature reduction, drives the material into the martensitic phase, with its greatly increased flexibility. According to this preferred embodiment, use is made of an SMA rod with a transition temperature below body temperature. A mechanism is provided for driving the rod into the delivery tube, and the stress applied to the rod as it is pushed into the curve of the delivery tube, switches it into its martensitic phase according to the pseudo-elasticity effect, enabling it to negotiate the curve readily. On emerging from the curve, when the stress disappears, the rod reverts to its original stiff austenitic phase, and is deployed between the pedicle screws. That way, there are no heating or cooling considerations to be made, other than the selection of the correct transition point temperature. In this respect, care must be taken, since considerable stress is applied to the rod when deployed, by the natural flexing motions of the spine. If the transition temperature is not chosen correctly, the rod may be driven into its pseudo-elastic region again by these bodily forces, thereby nullifying its function in preventing intervertebral motion. By use of a material with an upper transition point sufficiently below the body temperature, it is ensured that even with the maximum forces applied by spinal motion, the rod will not get to its pseudo-elastic state. Alternatively and preferably, the rod can be cooled before insertion such that the stress of insertion will send it to its pseudo-elastic state, but the stress of regular use in situ at body temperature will not.

There is thus provided in accordance with a preferred embodiment of the present invention, a vertebral fusion system for connecting at least two vertebrae in the spine of a subject, comprising a fastener attached to each of the at least two vertebrae, and a rod for connecting between the fasteners, wherein the rod comprises a material having shape memory. The fasteners are preferably pedicle screws.

In accordance with another preferred embodiment of the present invention, the material having a shape memory is a shape memory alloy. Preferably, this shape memory alloy is a Nitinol alloy. Alternatively and preferably, the material having a shape memory may be a shape memory polymer.

In any of the above described vertebral fusion systems, the shape memory material preferably has a transition range of temperatures, the rigidity of the material below the transition range of temperatures being substantially less than that above the transition range of temperatures. This transition range of temperatures is preferably below body temperature, and could be in the range between −5° C. and 32° C., or between 15° C. and 25° C.

There is further provided in accordance with yet another preferred embodiment of the present invention, the vertebral fusion system as described above also comprises a curved insertion tube for delivery of the connecting rod subcutaneously through an incision made in the skin of the subject. The insertion rod is cooled to a temperature preferably below body temperature before insertion. The system may also preferably comprise a cooler for reducing the temperature of the rod before insertion. Additionally, the insertion tube may also preferably be cooled to a temperature below body temperature.

In accordance with still another preferred embodiment of the present invention, in the vertebral fusion system described above, the insertion tube also comprises a pushing device for forcing the rod down the insertion tube. The pushing device may preferably be a screw.

There is further provided in accordance with still another preferred embodiment of the present invention, a vertebral fusion system as described above, for use when the spine of the subject has curvature, and in which the connecting rod has a memory shape above the transition range of temperatures having a curve matched to that of the vertebrae to be connected in the region of the curvature of the spine, such that the rod connects more than two vertebrae in the spine.

In any of the above described embodiments, the rod may preferably comprise a plurality of thin rods.

There is also provided in accordance with a further preferred embodiment of the present invention, a method of inserting a vertebral fusion rod into the back of a subject, comprising the steps of:
(i) inserting a curved delivery tube into the back of the subject, such that the inserted end of the delivery tube faces a direction substantially parallel to the spine,
(ii) providing a rod of shape memory material, the material having a transition range of temperatures, the rigidity of the material below the transition range of temperatures being substantially less than that above the transition range of temperatures,
(iii) cooling the rod to below the transition range of materials,
(iv) inserting the cooled rod into the back of the subject through the curved delivery tube, such that it lies substantially parallel to the spine, and
(v) allowing the rod to warm up to above the transition range of temperatures.

In the above described method, the transition range of temperatures is preferably below body temperature, and could be in the range between −5° C. and 32° C., or between 15° C. and 25° C.

Additionally, the step of cooling the rod is preferably performed using an external cooler. Furthermore, the method may also preferably comprise the step of cooling the insertion tube to a temperature below body temperature.

In accordance with still another preferred embodiment of the present invention, in the above described method, the step of inserting the cooled rod into the back of the subject may be performed by means of a pushing device for forcing the rod down the insertion tube. The pushing device may preferably be a screw.

In all of the above described methods, the curved delivery tube for insertion of the connecting rod is inserted subcutaneously through an incision made in the skin of the subject, such that the method is minimally invasive.

In accordance with yet another preferred embodiment of the present invention, there is also provided a method as described above, for use on a subject with a spine having curvature, the method also comprising the steps of:
(i) imaging the spine to determine a curved path of predefined features on the spine in the region where the vertebral fusion rod is to be installed,
(ii) bending the rod at a temperature above the transition range of temperatures into a curved shape that matches the curved path,
(iii) annealing the rod such that the curved shape is set as its memory shape,
(iv) cooling down the rod such that it loses the memory shape,
(v) inserting the rod into the back of the patient through the delivery tube, and
(vi) allowing the rod to warm up above the transition range of temperatures, such that it regains the curved memory shape.

The predefined features on the spine may preferably be the heads of pedicle screws inserted into vertebrae of the spine.

In any of the above described methods, the rod may preferably comprise a plurality of thin rods.

There is further provided in accordance with yet another preferred embodiment of the present invention, an insert for implanting in the body of a subject, the insert comprising a shape memory material, and wherein the insert has a final shape after insertion in the body essentially the same as its shape before insertion. The shape memory material is preferably such that the flexibility of the insert is increased during insertion, such that the insert changes its shape during insertion.

In accordance with still another preferred embodiment of the present invention, there is provided a method of inserting an insert into the body of a subject comprising the steps of:
(i) providing an insert having a predefined shape, the insert comprising a shape memory material,
(ii) changing the temperature of the insert such that its predefined shape can change,
(iii) inserting the insert into the body of the subject while its predefined shape is changed, and
(iv) allowing the insert to regain its predefined shape within the body of the subject. Furthermore, according to this method, the change of temperature of the insert is preferably such that the rigidity of the insert decreases, the decreased rigidity enabling the predefined shape to change during insertion.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Reference is now made to FIG. 1, which illustrates schematically a sectional side view of a number of vertebrae of a spine 10 situated beneath the skin 8 of a subject, with an adjacent pair of vertebrae 12, 14, fused together using two pedicle screws 16, 18 and a connecting rod 20. The spinous process 17 of each vertebra, the vertebrae themselves, and the disc 19 are shown schematically in FIG. 1. It is to be understood that there is an additional connecting rod between pedicle screws inserted into the other lateral side of the spine, and unseen in the side view of FIG. 1.

Figure 2:
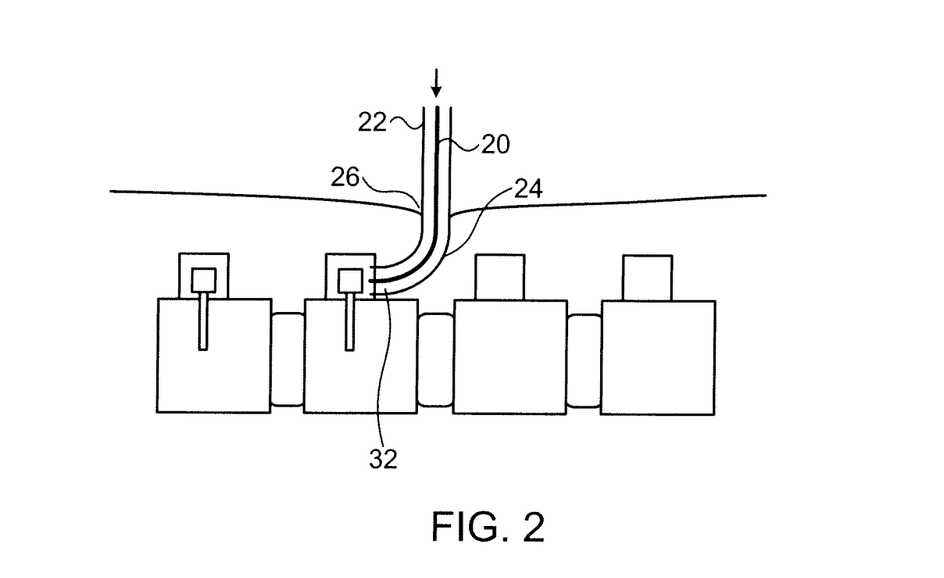
FIG. 2 is a schematic illustration of an SMA vertebral connecting rod, according to a preferred embodiment of the present invention, being inserted into the back of a subject through a curved insertion tube.

Reference is now made to FIG. 2 which schematically illustrates an SMA rod 20, according to a preferred embodiment of the present invention, constructed and operative as a vertebral connecting rod. The rod is shown being inserted through a curved insertion tube 22, while being held at a temperature below its transition point. At such a temperature, the rod is sufficiently flexible to pass round the curved section 24 of the insertion tube 22. The insertion tube 22 is deployed in position in the back of the subject through a minimally invasive incision 30. According to the preferred embodiment shown in FIG. 2, the insertion of the rod is performed in a generally perpendicular direction to the spine axis. The front of the rod is preferably pointed to facilitate penetration of the soft tissue.

In order to be compatible with the body temperature, the transition temperature of the SMA should preferably be in the range of −5° C. to 30° C., with an optimal range being 15° C. to 25° C. Suitable SMA's for constructing the rod thereof include a range of alloys known as NiTinol, having nearly equal ratios of nickel and titanium, and which have been widely used in many applications, including medical applications such as in heart valves, guide wires, stents, bone cores, implants and plates. In addition, a range of copper-zinc-aluminium alloys are also suitable SMA materials. After being deformed, the material remembers its original annealed shape and returns to that original shape when heated above the shape transition temperature.

According to a first preferred embodiment, the curved tube 22 is cooled, especially close to the beginning 24 of the curved region, to below the transformation temperature of the SMA, such that the rod material structure undergoes a phase change from austenitic to martensitic as it passes along the tube. According to a second preferred embodiment, the tube need not be cooled but the rod itself is sufficiently pre-cooled for it to maintain a sub-transformation temperature during its passage through the tube. In the martensitic phase, the rod achieves a level of flexibility which allows it to accommodate to the shape of the curved tube as it is inserted therein. Since the exit section 32 of the tube is straight, the rod leaves the tube parallel to the spine axis, and close to its original straight shape. As the rod is pushed out of the tube, it becomes heated up by the surrounding body tissue and changes back into its austenitic phase, regaining both the original rod strength, and its original shape.

The rod, whose front end is preferably pointed for ease of insertion and for causing less tissue trauma, is progressively pushed out of the tube until its front end reaches the position of the screw head at the pedicle further from the point of insertion. The rod length is predetermined such that it bridges between the two adjacent pedicle screws when deployed. Fastening of the rod to the pedicle screw heads can be performed by any of the conventionally used techniques known in the art, such as by fastening by means of set screws into slots cut into the top of the pedicle screw heads. The insertion tube is preferably removed from the body tissue only once the rod has been fastened, such that the tube provides extra support for the pedicle screw and rod while the fasteners are being tightened.

Figure 3:
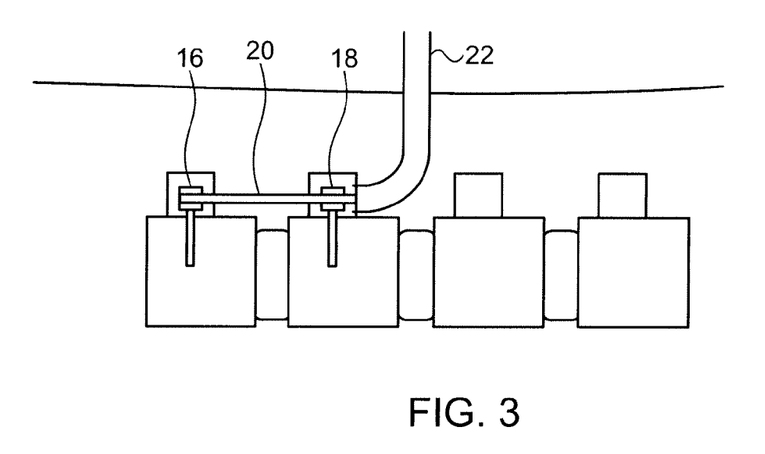
FIG. 3 is a schematic illustration of the SMA connecting rod of FIG. 2 fully deployed between pedicle screw heads of adjacent vertebrae.

Reference is now made to FIG. 3, which illustrates the connecting rod 20 of FIG. 2, after it has been fully deployed from the insertion tube 22, and in its intended position between the pedicle screws 16, 18, ready for attachment thereto.

Figure 4:
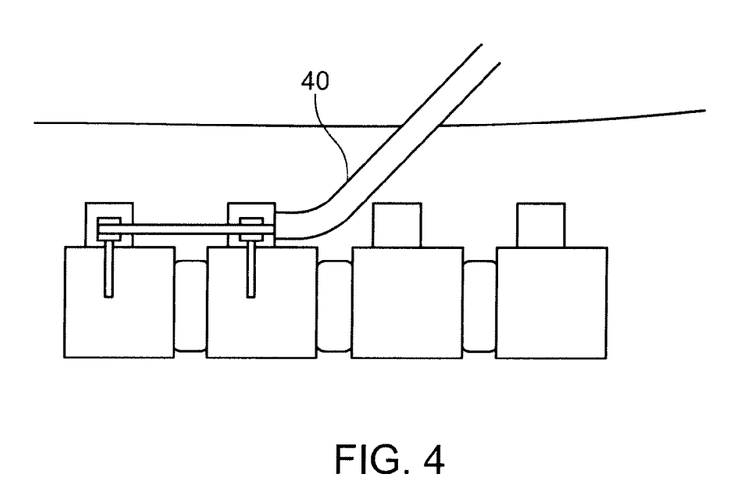
FIG. 4 is a schematic illustration of a more gently curved insertion tube disposed in an angled position in the back of the patient, according to another preferred embodiment of the present invention.

Reference is now made to FIG. 4, which is a schematic illustration similar to that of FIG. 2, but with an insertion tube 40 with a less sharply curved delivery end. The rod is then inserted at an acute angle to the spinal direction. Although the insertion tube of FIG. 4 requires a longer subcutaneous insertion passage than that of FIG. 2, and thus, for instance, cannot generally be inserted through the same incision as was made for the pedicle screws (though in some cases, a single incision can be made if the soft tissues can be sufficiently stretched), such a less sharply curved tube may be necessary for use with SMA's with a limited maximum strain. The NiTinol materials, for instance, generally have a maximum strain level of 8%, thus limiting the sharpness of the curve that they can negotiate when in their martensitic state.

Figure 8:
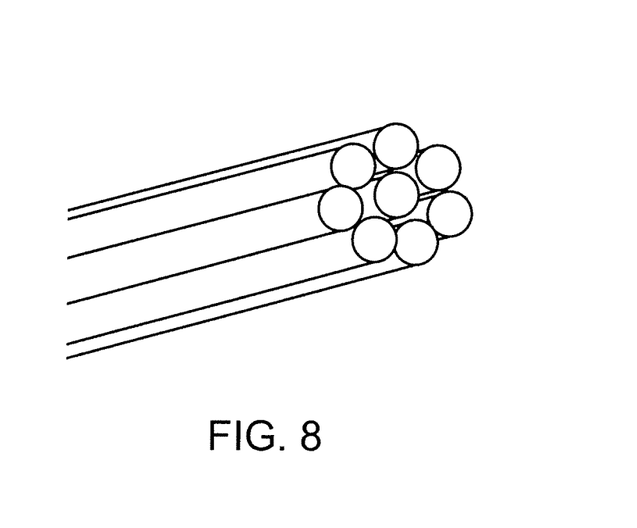
FIG. 8 shows an example of a stranded rod for use in any of the embodiments of the present invention.

Although it is conventional in the art to use a single rod to connect the pedicle screws on each side of the spine, and that is the manner in which the embodiments of this application have been so far described, it is to be understood that the invention is not meant to be limited to such a situation, but that each pair of pedicle screws may be connected by several thinner rods, forming a stranded pedicle screw connection link made up of several thinner wire-like rods. The term rod, as used and as claimed in this application, is understood to include also such thinner wire-like rods, and also such complete stranded rods. Such an embodiment has the advantage that the above-mentioned strain limit of 8% for currently available materials, may be more readily maintained when inserting thinner rods through the curved tube, as compared with a single thicker rod. The thinner wire-like rods can be inserted in the same manner as described hereinabove, as shown in FIGS. 2 to 4, one after another, and then all connected to the pedicle screw heads in the conventional manner. Alternatively and preferably, the stranded connecting rod may be inserted as one unit, with each strand of the rod undergoing its own strain during insertion. The stranded rod may also preferably be twisted to maintain integrity. A stranded connecting rod may not provide such rigid support as a solid connecting rod, but this may be advantageous for applications where slight motion preservation is desired between vertebrae. A preferred example of such a stranded rod for use in any of the embodiments of the present invention is shown schematically in FIG. 8 hereinbelow.

Figure 5:
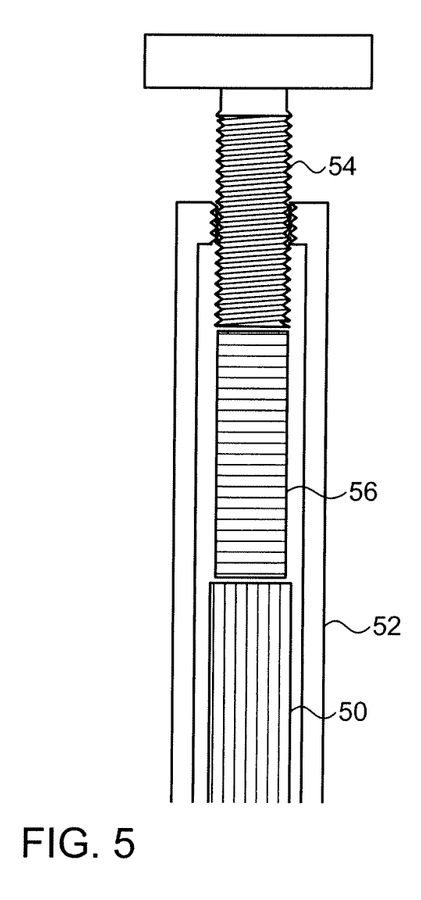
FIG. 5 is a schematic illustration of a screwing mechanism used to insert the connecting rod shown in FIG. 2, according to another preferred embodiment of the present invention.

Reference is now made to FIG. 5, which illustrates schematically a preferred embodiment of a device for pushing an SMA rod 50 into the insertion tube 52. Only the top end of the insertion tube is shown in FIG. 5. The pushing device must have means of maintaining the force on the rod even after its extremity has entered the curved delivery end of the tube and would no longer be directly accessible to a straight screw. In the preferred embodiment shown in FIG. 5, this can be accomplished by means of a screw drive mechanism 54 attached to the top end of the tube 52. The rod is inserted in a controlled manner by rotating the lead screw. A flexible drive shaft element 56 is preferably used to transfer the drive force to the rod even as it negotiates the curve. However, any suitable mechanical pushing device may equally be used. The SMA rod is made to be a good fit in the insertion tube such that when the rod is in its flexible state, it will be contained by the walls of the tube and prevented from kinking, such that it will progress undisturbed through the whole tube.

Figure 6:
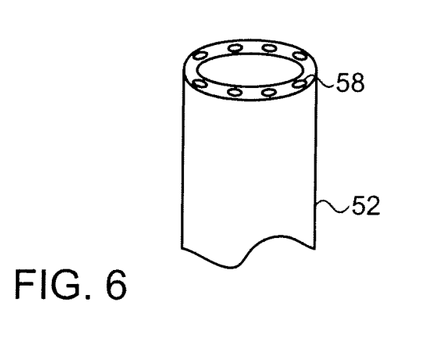
FIG. 6 is a schematic cut-away drawing of one preferred method of cooling the insertion tube.

In order to keep the rod in its cooled martensitic state when put into the insertion tube, according to another preferred embodiment of the present invention, the tube may be cooled externally. This may be done simply by passing cooling fluid through channels built into the insertion tube, or through cooling coils wrapped around the insertion tube, or even by blowing cold gas over its outer surface. Reference is now made to FIG. 6 which schematically illustrates one such solution, comprising a number of fluid cooling passages 58 built into the walls of the insertion tube 52, though it is to be understood that this is only an exemplary method of cooling the tube, and any other suitable method is equally acceptable.

There is a problem in performing multilevel vertebral fusion, since, because of spinal curvature or distortion, the pedicle screw heads do not generally align in a straight line. Even the use of self aligned screw heads that have a joint that can accommodate some deviations from the straight line is usually not sufficient to ensure that the rod is captured by all of the pedicle screw heads. The use of a straight connecting rod to connect more than one level might therefore be ineffective. When conventional open back surgery is performed, the surgeon can visually match a multi-level rod to the desired path between the pedicle screw heads, using regular hand tools such as pliers to bend the rod accordingly. With the Dynesy® system, such vertebra to vertebra flexibility is built into the system using separate rods. However, using minimally invasive procedures, such as the SEXTANT™ or PathFinder™ systems, each level generally has to be performed separately with its own set of incisions.

Figure 7:
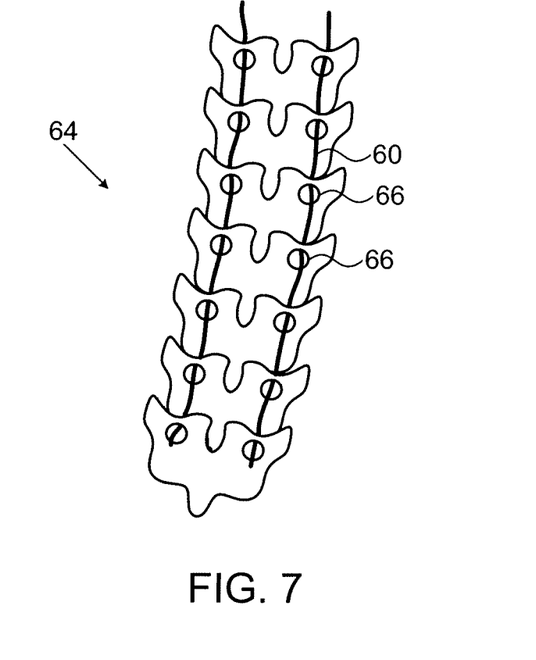
FIG. 7 is a plan schematic illustration of several vertebral levels showing a multi-level connecting rod passing through the heads of several non-linearly located pedicle screws.

Reference is now made to FIG. 7 which illustrates an SMA connecting rod 60 which connects more than one level of vertebrae, according to another preferred embodiment of the present invention. According to this embodiment, multi-level rod insertion using the minimally invasive procedures of a single rod insertion point becomes possible by using the shape memory properties of the rod. In FIG. 7, there is shown schematically a laterally curved spine 64, such as that of a scoliosis patient. Pedicle screw heads 66 are shown of pedicle screws inserted into the vertebrae. The screw head path is seen to be curved, such that a single straight rod would not pass through them. A plan of the pedicle screw head path is obtained by means of fluoroscopic images, and an SMA rod 60, long enough to bridge all of the levels to be fused, is prepared. The rod is then bent, before insertion, into the required shape to match, as best as possible, the pedicle screw head path obtained from the images. The SMA rod is then annealed by the methods known in the art, to set that preplanned bent shape into the material in its austenitic phase. The rod is then cooled before insertion such that it transforms into its flexible martensitic phase, and can readily be pulled out straight. In this cooled condition, the straightened rod is inserted into the patient's spinal region at one end of the region to be fused, through the delivery tube, as shown in the above described embodiments of the present invention. On heating up to body temperature, the shape memory effect of the SMA rod causes it to regain its preplanned bent shape, to match the pedicle screw head path. Although it is unlikely that the regained shape will lie exactly on the pedicle screw head slots, the rod should now be close to those desired locations, and it will be a simple task for the surgeon to visually locate the rod through each of the pedicle screw incisions and to push aside the soft tissue to hook it into place in each screw head slot, if it is not already there.

Although FIG. 7 shows an example of a spine with a single curvature, it is to be understood that the method may also be used to connect zig-zag shaped spinal curvature. Furthermore, although this embodiment has been described in FIG. 7 for connecting laterally curved spines, it is to be understood that the same technique can be used for connecting and fusing vertebrae having abnormal curvature in any other plane of the spine.

Though the present invention has been described hereinabove using an SMA as the rod material, it is to be understood that any other material which undergoes a change in flexibility at just below body temperature, and which shows shape memory effects, could equally well be used.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

I claim:

1. A vertebral fusion system for connecting at least two vertebrae in the spine of a subject, comprising:
   at least two fasteners, each of said fasteners being adapted to be attached to a vertebra;
   a rod comprising a material having shape memory for connecting between said at least two fasteners, said material having a transition range of temperatures below body temperature, the rigidity of said material below said transition range of temperatures being substantially less than that above said transition range of temperatures, said rod having a shape above said transition range of temperatures, preplanned to match a path between said at least two fasteners; and
   a curved insertion tube with its distal end directed at the path between said at least two fasteners, for delivery of said connecting rod subcutaneously through an incision made in the skin of the subject, said curved insertion tube having a temperature below said transition range of temperatures, and a shape different from the shape of said connecting rod above said transition range of temperatures.

2. A vertebral fusion system according to claim 1 and wherein said fasteners are pedicle screws.

3. A vertebral fusion system according to claim 1, wherein said material having a shape memory is a shape memory alloy, or a shape memory polymer.

4. A vertebral fusion system according to claim 3 and wherein said shape memory alloy is a Nitinol alloy.

5. A vertebral fusion system according to claim 1 and wherein said transition range of temperatures is between −5° C. and 32° C.

6. A vertebral fusion system according to claim 1 and wherein said transition range of temperatures is between 15° C. and 25° C.

7. A vertebral fusion system according to claim 1 and also comprising a cooler for reducing the temperature of said rod before insertion.

8. A vertebral fusion system according to claim 1 and wherein said insertion tube also comprises a pushing device for forcing said rod down said insertion tube.

9. A vertebral fusion system according to claim 8 and wherein said pushing device is a screw.

10. A vertebral fusion system according to claim 1, and wherein said spine of said subject has a curvature, and said rod has a memory shape above said transition range of temperatures having a curve matched to that of said vertebrae to be connected in the region of said curvature, such that said rod connects more than two vertebrae in said spine.

11. A vertebral fusion system according to claim 1, and wherein said rod comprises a plurality of thin rods.

12. A vertebral fusion system according to claim 1, said insertion tube having a cooling system for reducing its temperature below said transition range of temperatures.

13. A vertebral fusion system according to claim 12, said cooling system comprising any one of channels built into said insertion tube, or cooling coils wrapped around said insertion tube, or a blower flowing cold gas over the outer surface of said insertion tube.

14. A vertebral fusion system according to claim 1, wherein said preplanned shape of said rod is determined from fluoroscopic images of said path between said at least two fasteners.

15. A vertebral fusion system for connecting at least two vertebrae in the spine of a subject, comprising:

at least two fasteners, each of said fasteners being adapted to be attached to a vertebra;

a rod comprising a material having shape memory for connecting between said at least two fasteners, said material having a transition range of temperatures below body temperature, the rigidity of said material below said transition range of temperatures being substantially less than that above said transition range of temperatures, said rod having a shape above said transition range of temperatures, preplanned to match a path between said at least two fasteners; and a curved insertion tube with its distal end directed at the path between said at least two fasteners, for delivery of said connecting rod subcutaneously through an incision made in the skin of the subject, said curved insertion tube having a temperature below said transition range of temperatures, and a shape different from the shape of said path between said at least two fasteners.

* * * * *